United States Patent [19]

Zweig

[11] Patent Number: 5,590,170
[45] Date of Patent: Dec. 31, 1996

[54] X-RAY INSPECTION SYSTEM

[75] Inventor: Gilbert Zweig, Morris Plains, N.J.

[73] Assignee: Glenbrook Technologies, Morris Plains, N.J.

[21] Appl. No.: 328,465

[22] Filed: Oct. 25, 1994

Related U.S. Application Data

[63] Continuation-in-part of Ser. No. 46,604, Apr. 12, 1993, abandoned.

[51] Int. Cl.$^6$ ............................................. G01N 23/04
[52] U.S. Cl. ........................................... 378/63; 378/98.5
[58] Field of Search ......................................... 378/63, 98.5

[56] References Cited

U.S. PATENT DOCUMENTS

| | | |
|---|---|---|
| 4,246,607 | 1/1981 | Vipverberg .............................. 378/98.5 |
| 4,670,896 | 6/1987 | Klausz ..................................... 378/98.5 |
| 4,890,313 | 12/1989 | Lam et al. . |
| 4,894,855 | 1/1990 | Kresse . |
| 4,907,252 | 3/1990 | Aichinger ................................. 378/63 |
| 4,974,249 | 11/1990 | Zweig . |
| 4,995,068 | 2/1991 | Chou et al. . |
| 5,038,369 | 8/1991 | Nishiki . |
| 5,113,425 | 5/1992 | Zweig . |
| 5,119,409 | 6/1992 | Nields et al. . |
| 5,127,032 | 6/1992 | Lam et al. . |

FOREIGN PATENT DOCUMENTS 54-158984  12/1979  Japan .

*Primary Examiner*—Craig E. Church
*Attorney, Agent, or Firm*—Mathews, Woodbridge & Collins

[57] ABSTRACT

This invention relates to a high resolution X-ray imaging device for congruently combining an optical image from a video system with a fluoroscopic X-ray image from a fluoroscopic imaging system. An X-ray beam is directed towards a predetermined position of an object to be inspected and an X-ray image is received at the fluoroscopic imaging system for generating the fluoroscopic X-ray image. A mirror is positioned between the fluoroscopic imaging system and the X-ray beam. The X-ray beam passes substantially unattenuated through the mirror. Preferably, the mirror is formed of a composition having elements with an atomic number of less than 14. An optical image of the predetermined location of the object is reflected off of the mirror. The optical image and the fluoroscopic X-ray image can be combined into a superimposed image.

3 Claims, 2 Drawing Sheets

X-RAY INSPECTION SYSTEM

This application is a continuation-in-part of U.S. Ser. No. 08/046,604 filed Apr. 12, 1993, now abandoned.

BACKGROUND OF THE INVENTION

1. Field of the Invention

This invention relates to a high resolution X-ray imaging apparatus for combining an optical image from a video system with a fluoroscopic image from an X-ray system.

2. Description of the Related Art

It is known that X-ray inspection techniques are used for quality control in the production of electronic components, such as integrated circuits, multi-layer printed circuit boards and surface mounted components. Conventional X-ray inspection systems produce an X-ray image of the object being inspected. In addition, X-ray inspection systems are used for producing images of patients during medical treatments.

U.S. Pat. No. 4,995,068 describes a radiation therapy imager for providing X-ray images of a patient while being treated on a radiation therapy machine for the purpose of verification and monitoring of the position of the patient. A fluoroscopic plate produces a fluoroscopic image of the patient. The fluoroscopic plate has a detection resolution of 1.6 lp/mm. A first remote camera picks up the fluoroscopic image. An image of a simulator radiograph is picked up by a second remote camera. A remote console has the capability of receiving input from both the first and second cameras and for aligning the fluoroscopic image with the radiograph film image. The technology described in U.S. Pat. No. 4,995,068 has the shortcoming that the observer is viewing two different objects from two different locations. Also, the resolution of the images from a fluoroscopic plate is inadequate for electronic component inspection.

U.S. Pat. Nos. 4,890,313 and 5,127,032 describe X-ray imaging systems for indicating alignment of X-ray beams with patient areas to be inspected. X-rays are projected at a 90° angle to each other. A fluorescence screen is excited to emit light after receiving the X-rays. A thin deflection mirror is used to locate a video camera out of the path of the X-rays but in position to receive and record X-ray images on the fluorescence screen.

U.S. Pat. Nos. 4,974,249 and 5,113,425 issued to the inventor of this disclosure describe an X-ray inspection system for producing both film and fluoroscopic images of electronic components and assemblies therefor. An X-ray cabinet includes an X-ray tube and a slidable drawer for supporting the object to be inspected and film. An aperture is formed in the drawer to the X-ray tube. A fluoroscopic imaging device attaches to the slidable drawer for converting an X-ray image of the object to a fluoroscopic X-ray image. An output of the fluoroscopic imaging device is optically coupled to a video monitor. The fluoroscopic imaging device includes a thinly coated radioluminescent phosphor plate optically coupled to the input of an image intensifier. A microchannel plate image intensifier is used for providing a relatively high resolution image of the object.

Japanese Patent No. 54158984 describes an X-ray fluoroscopic inspection apparatus. X-rays are transmitted through a mirror. A camera picks up the transmitted X-rays after they pass through the object to be inspected. Visible rays from the object to be inspected reflect off the mirror and are picked up by an IVT camera. This patent has the drawback of scattering the X-rays with the mirror, thereby making the system unsuitable for detecting flaws in electronic components.

Conventional mirrors are formed of silica (glass) and oxygen. Silica has an atomic number of 14. When silica is used in the path of an X-ray beam, the silica absorbs the X-rays and re-emits secondary X-rays which effect is referred to in the prior art as scattering or Compton scattering. Scattering has the effect of formation of image noise which degrades the X-ray or fluoroscopic image. The degradation of the X-ray image is disadvantageous for high resolution inspection systems which congruently combine an optical image and an X-ray image of an object to be inspected.

Of possible general relevance are: U.S. Pat. Nos. 4,894,855, 5,038,369, and 5,119,409 directed to X-ray imaging systems.

For certain applications, such as inspection of electronic components, it is often desirable to optically view the object. In addition to X-ray inspection of the object, optical inspection can be used for determining various defects in the electronic components. An inspection system which combines an optical image from a video system with an X-ray image from an X-ray system in which both images are generated at the same location of an object to be inspected is not believed to be found in the prior art. It is desirable to provide a high resolution inspection system which congruently combines optical images and X-ray images of an object to be inspected.

SUMMARY OF THE INVENTION

Briefly described, the invention comprises an X-ray inspection system for congruently combining a fluoroscopic X-ray image with an optical image of the same object. An X-ray tube projects an X-ray beam towards the object which passes substantially unattenuated through an angled mirror to the object. A fluoroscopic imaging device is positioned below the object for converting the X-ray image into a fluoroscopic X-ray image. A second video camera is directed towards the angled mirror for receiving an optical image of the object to be inspected. A first video camera is directed towards the fluoroscopic X-ray image output of the X-ray image convertor. A video monitor receives the fluoroscopic X-ray image and the optical image.

In accordance with the teachings of the present invention, magnification means can be provided for simultaneously magnifying the fluoroscopic X-ray image and the optical image to the same magnification. Preferably, the fluoroscopic imaging device and video camera produce images with a resolution of at least 5 lp/mm.

Preferably, the mirror is formed of a composition which is transparent to the X-ray for preventing scattering and image noise of the X-ray image. It has surprisingly been found that a composition formed of boron carbide is transparent to X-rays used in the present X-ray system. The use of a mirror composition which is transparent to the fluoroscopic X-ray provides images which are noise-free and allows an operator of the inspection system to detect minute flaws in electronic components.

The invention may be more fully understood by reference to the following drawings.

DETAILED DESCRIPTION OF THE INVENTION

During the course of this description like numbers will be used to identify like elements according to the different figures which illustrate the invention.

Figure 1:
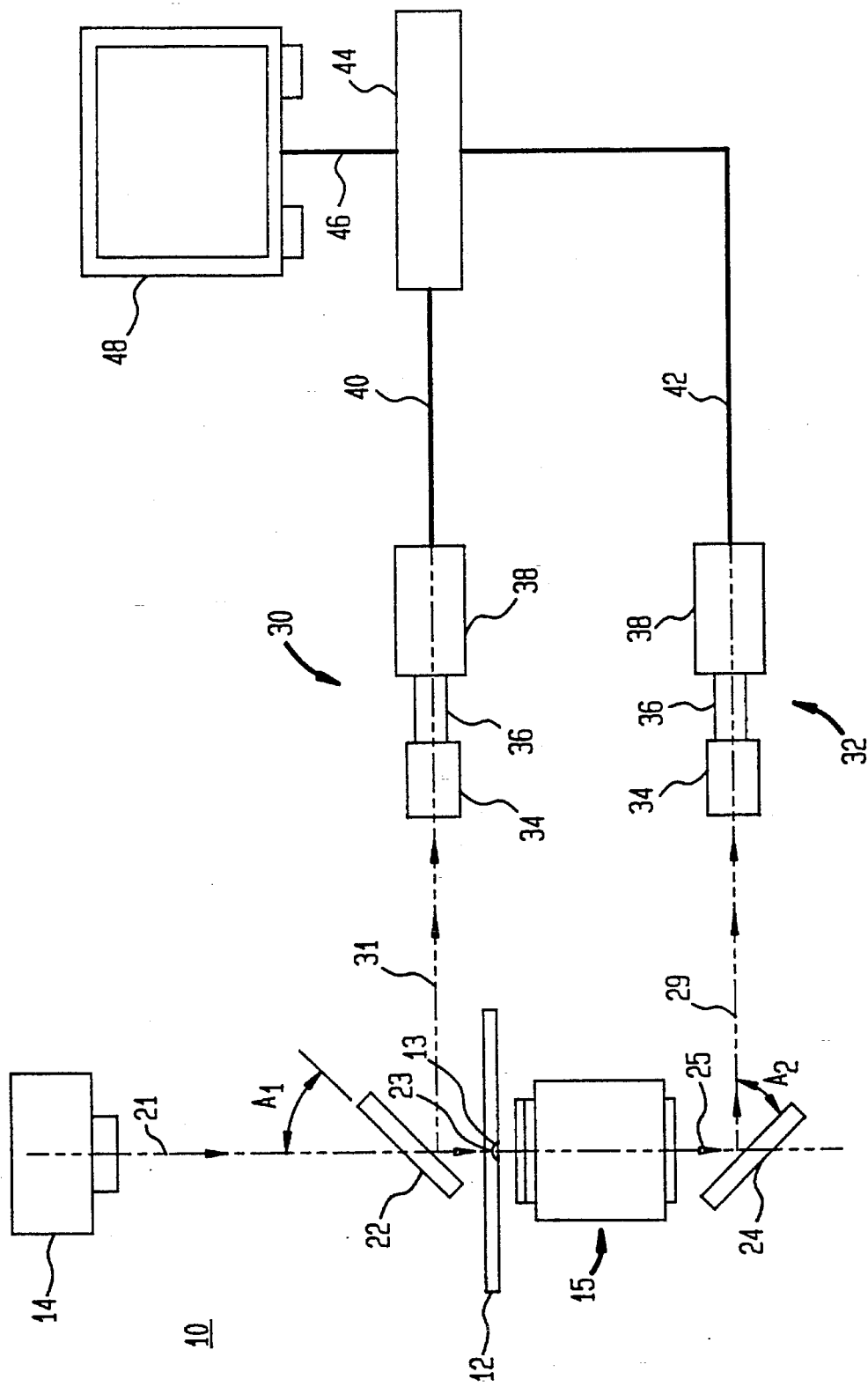
FIG. 1 is a schematic view of the X-ray inspection system of the present invention.

FIG. 1 is a schematic view of X-ray inspection system 10 in accordance with the principles of the present invention. Support member 12 supports an object to be inspected (not shown). Preferably, the object to be inspected includes electronic components and circuit boards therefor. In addition, semiconductor element bonding can be inspected including die attachment, placement of inner lead wires and lid seal integrity. It will be appreciated that other objects, for example biological specimens, could be inspected in accordance with the teachings of the present invention.

Figure 2:
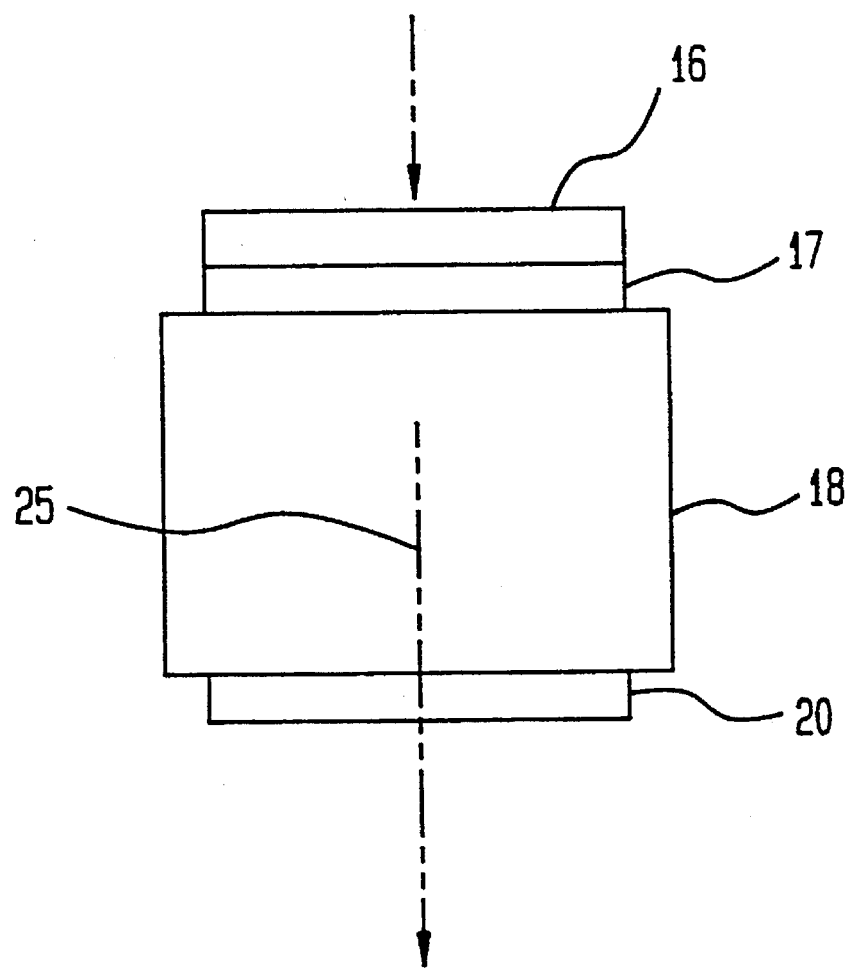
FIG. 2 is a perspective view of the fluoroscopic imaging system shown in FIG. 1.

Support member 12 includes an aperture 13 positioned above the fluoroscopic imaging system 15. FIG. 2 illustrates fluoroscopic imaging system 15 which includes a luminescent phosphor coating 16 coupled to fiber optic input face plate 17. Fiber optic input face plate 17 is located adjacent microchannel plate intensifier 18. Fiber optic output face plate 20 receives the fluoroscopic X-ray image generated by fluoroscopic imaging system 15. Fluoroscopic imaging system 15 can be of the type described in U.S. Pat. No. 4,974,249 issued to the same inventor as this disclosure, and incorporated by reference into this application.

X-ray tube 14 projects an X-ray beam 21 toward position 23 of support member 12. X-ray beam 21 passes substantially unattenuated through mirror 22 to position 23 of support member 12. X-ray beam 21 passes through the object to be inspected and excites luminescent phosphor coating 16. Mirror 22 is formed of substantially thin glass for providing minimal X-ray opacity. Preferably, luminescent phosphor coating 16 is substantially near the object to be inspected so that the geometric magnification factor of the X-ray shadow falling on the phosphor is about unity. Luminescent phosphor coating 16 is relatively thin in coating thickness for achieving high resolution. Microchannel plate intensifier 18 amplifies output light 25 from luminescent phosphor coating 16. Preferably, the amplified fluoroscopic X-ray image produced by microchannel plate intensifier 18 has high resolution and a magnification of unity. Fluoroscopic imaging system 15 has a resolution in the range of about 5 to about 15 lp/mm of the X-ray image. Most preferably, a resolution of at least about 10 lp/mm is produced by fluoroscopic imaging system 15.

Output 25 of fluoroscopic imaging system 15 is directed to mirror 24 positioned directly below the fluoroscopic imaging system 15. Mirror 24 is positioned at angle $A_2$ from vertical for directing output 29 of microchannel plate intensifier 18 to video camera system 32. Preferably, angle $A_2$ is about $-45°$ from vertical. It will be appreciated that other angles of mirror 24 can be used in the present invention.

An optical image of the object to be inspected at position 23 of support member 12 is reflected off mirror 22 as input 31 to video camera system 30. Mirror 22 is positioned at an angle $A_1$ from vertical for directing the optical image of the object to be inspected to video camera system 30. Preferably, angle $A_1$ is about $45°$ from vertical. It will be appreciated that other angles of mirror 22 can be used in the present invention.

Video camera system 30 optically views the object to be inspected at a magnification greater than unity which can be 5 to 30 times. Preferably, video camera system 30 has a resolution of at least about 5 to about 15 lp/mm. Video camera system 32 views the fluoroscopic X-ray image of the object at the same magnification and orientation as video camera system 30 views the optical image of the object to be inspected.

Video camera systems 30 and 32 can include an extender 36 positioned between lens 34 and video camera body 38. Preferably, extender 36 is formed of a hollow tube. Magnification of the fluoroscopic X-ray image and the optical image of the object to be inspected can be increased or decreased simultaneously by varying the length of extender 36. For example, if lens 34 has a focal length of 50 mm and an extender 36 with a length of 20 mm is positioned between video camera body 38 and lens 34, the image from video camera body 38 will be magnified approximately 15 times.

Video output 40 of video camera system 30 and video output 42 of video camera system 32 can be mixed in video mixer 44 with conventional methods as are known in the art. Video mixer 44 is optically coupled to video display 48. Video mixer 44 allows either video output 40 or video output 42 to be inputed as mixer input 46 to video display 48 and displayed one at a time on video monitor 48. Output 40 can be used to correctly align X-ray beam 21 with the desired portion of the object to be inspected. Video mixer 44 can also superimpose video output 40 on video output 42 and provide the superimposed image as mixer input 46 to video monitor 48.

The X-ray inspection system 10 of the present invention has the advantage of permitting simultaneous inspection of objects with optical and fluoroscopic X-ray inspection at the same predetermined location of the object. The optical and X-ray fluoroscopic images of the object can be congruently superimposed on each other on a video monitor. The superimposed images can be used in a number of applications. For example, the ability to optically view a solder joint of an integrated circuit and then to precisely superimpose a fluoroscopic X-ray image of the same joint provides improved inspection capability for quality control.

Preferably, mirror 22 is formed of a material which is transparent to output 25 of fluoroscopic imagery system 15. Most preferably, mirror 22 is formed of a composition of elements having an atomic number less than about 14.

The preferred compositions for mirror 22 are formed of aluminum oxide having respective atomic numbers of 13 and 8 and beryllium oxide having respective atomic numbers of 4 and 8. A most preferred composition for mirror 22 is formed of boron carbide having respective atomic numbers of 5 and 6. It has been found that a mirror 22 formed of boron carbide is transparent in the voltage range of about 25 to about 95 kilovolts at which the X-ray voltage inspection system 10 operates.

While the invention has been described with reference to the preferred embodiment thereof, it will be appreciated by those of ordinary skill in the art that modifications can be made to the structure and form of the invention without departing from the spirit and scope thereof.

I claim:

1. An X-ray inspection system for electronic components including printed circuit boards comprising:

X-ray means for generating an X-ray beam for producing an X-ray image of an object, said object being said electronic component;

fluoroscopic imaging means for converting said X-ray image of said object to a fluoroscopic image, said fluoroscopic imaging means includes a thin luminescent phosphor means optically coupled to a microchannel plate image intensifier for providing a substantially high resolution fluoroscopic X-ray image of said object;

a first mirror positioned between said object and said X-ray means at an angle $A_1$, said mirror creating an optical image of said predetermined location of said object, said mirror being formed of a composition having at least one element with an atomic number of less than 14, said X-ray beam passes through said first mirror to said object and onto said fluoroscopic imaging means, said mirror being relatively transparent to said X-ray beam, first video camera means for viewing said fluoroscopic X-ray image and generating first video output of said fluoroscopic X-ray image;

second video camera means for viewing said predetermined location of said object as an optical image and generating second video output of said optical image; and video monitor means for receiving said first video output of said first video camera means and said second video output of said second video camera means, wherein said fluoroscopic X-ray image and said optical image appear at substantially equal magnification on said video monitor means, and said mirror is formed of boron carbide.

2. An X-ray inspection system for electronic components including printed circuit boards comprising:

X-ray means for generating an X-ray beam for producing an X-ray image of an object, said object being said electronic component;

fluoroscopic imaging means for converting said X-ray image of said object to a fluoroscopic image, said fluoroscopic imaging means includes a thin luminescent phosphor means optically coupled to a microchannel plate image intensifier for providing a substantially high resolution fluoroscopic X-ray image of said object;

a first mirror positioned between said object and said X-ray means at an angle $A_1$, said mirror creating an optical image of said predetermined location of said object, said mirror being formed of a composition having at lease one element with an atomic number of less than 14, said X-ray beam passes through said first mirror to said object and onto said fluoroscopic imaging means, said mirror being relatively transparent to said X-ray beam, first video camera means for viewing said fluoroscopic X-ray image and generating first video output of said fluoroscopic X-ray image;

second video camera means for viewing said predetermined location of said object as an optical image and generating second video output of said optical image; and video monitor means for receiving said first video output of said first video camera means and said second video output of said second video camera means, wherein said fluoroscopic X-ray image and said optical image appear at substantially equal magnification on said video monitor means, and said mirror is formed of aluminum oxide.

3. An X-ray inspection system for electronic components including printed circuit boards comprising:

X-ray means for generating an X-ray beam for producing an X-ray image of an object, said object being said electronic component;

fluoroscopic imaging means for converting said X-ray image of said object to a fluoroscopic image, said fluoroscopic imaging means includes a thin luminescent phosphor means optically coupled to a microchannel plate image intensifier for providing a substantially high resolution fluoroscopic X-may image of said object;

a first mirror positioned between said object and said X-ray means at an angle $A_1$, said mirror creating an optical image of said predetermined location of said object, said mirror being formed of a composition having at lease one element with an atomic number of less than 14, said X-ray beam passes through said first mirror to said object and onto said fluoroscopic imaging means, said mirror being relatively transparent to said X-ray beam, first video camera means for viewing said fluoroscopic X-ray image and generating first video output of said fluoroscopic X-ray image;

second video camera means for viewing said predetermined location of said object as an optical image and generating second video output of said optical image; and video monitor means for receiving said first video output of said first video camera means and said second video output of said second video camera means, wherein said fluoroscopic X-ray image and said optical image appear at substantially equal magnification on said video monitor means, and wherein said mirror is formed of beryllium oxide.

* * * * *